(12) United States Patent
Mourao et al.

(10) Patent No.: US 11,273,116 B2
(45) Date of Patent: Mar. 15, 2022

(54) STRIPED DENTIFRICE COMPOSITION COMPRISING ZINC

(71) Applicant: COLGATE-PALMOLIVE COMPANY, New York, NY (US)

(72) Inventors: Marcella F. Mourao, Sao Paulo (BR); Tilo Poth, Weinheim (DE); Fernanda Correa, Sao Paulo (BR)

(73) Assignee: Colgate-Palmolive Company, New York, NY (US)

( * ) Notice: Subject to any disclaimer, the term of this patent is extended or adjusted under 35 U.S.C. 154(b) by 28 days.

(21) Appl. No.: 14/983,709

(22) Filed: Dec. 30, 2015

(65) Prior Publication Data

US 2017/0189300 A1 Jul. 6, 2017

(51) Int. Cl.
| | |
|---|---|
| *A61K 8/73* | (2006.01) |
| *A61K 8/27* | (2006.01) |
| *A61Q 11/00* | (2006.01) |
| *A61Q 11/02* | (2006.01) |

(52) U.S. Cl.
CPC ............ *A61K 8/731* (2013.01); *A61K 8/27* (2013.01); *A61K 8/73* (2013.01); *A61Q 11/00* (2013.01); *A61Q 11/02* (2013.01); *A61K 2800/26* (2013.01); *A61K 2800/42* (2013.01); *A61K 2800/48* (2013.01)

(58) Field of Classification Search
CPC . A61K 8/731; A61K 8/73; A61K 8/27; A61K 2800/48; A61K 2800/42; A61K 2800/26; A61Q 11/00; A61Q 11/02
See application file for complete search history.

(56) References Cited

U.S. PATENT DOCUMENTS

| | | | | |
|---|---|---|---|---|
| 5,145,667 A | * | 9/1992 | Ibrahim | A61K 8/24 424/52 |
| 5,980,870 A | | 11/1999 | Baik et al. | |
| 6,221,340 B1 | * | 4/2001 | Yu | A61K 8/22 424/49 |
| 6,315,986 B1 | | 11/2001 | Wong et al. | |
| 6,447,758 B1 | * | 9/2002 | Carale | A61K 8/463 424/54 |
| 6,706,256 B2 | * | 3/2004 | Lawlor | A23G 3/36 424/440 |
| 8,221,722 B2 | | 7/2012 | Baig et al. | |
| 2007/0025928 A1 | * | 2/2007 | Glandorf | A61K 8/20 424/49 |
| 2007/0122358 A1 | * | 5/2007 | Wang | A61K 8/25 424/52 |
| 2007/0122359 A1 | * | 5/2007 | Wang | A61K 8/25 424/52 |
| 2008/0152599 A1 | * | 6/2008 | Brignoli | A61K 8/0237 424/49 |
| 2008/0247968 A1 | | 10/2008 | Sagel | |
| 2008/0248073 A1 | * | 10/2008 | Gantenberg | A61K 8/02 424/401 |
| 2012/0042893 A1 | | 2/2012 | Campbell et al. | |
| 2013/0064779 A1 | | 3/2013 | Yamane et al. | |
| 2013/0095159 A1 | | 4/2013 | Boyd et al. | |
| 2013/0330283 A1 | | 12/2013 | Vogt et al. | |
| 2015/0275132 A1 | * | 10/2015 | Denutte | A61K 8/35 424/49 |
| 2015/0335539 A1 | | 11/2015 | Prencipe et al. | |

FOREIGN PATENT DOCUMENTS

| | | |
|---|---|---|
| WO | WO 2014/059678 | 4/2014 |
| WO | WO 2015/065502 | 6/2015 |

OTHER PUBLICATIONS

Anonymous, 2000, "Striped Dentifrice," 435:1174.
International Search Report and Written Opinion of the International Searching Authority in International Application No. PCT/US2016/068719, dated May 12, 2017.

* cited by examiner

*Primary Examiner* — Lezah Roberts

(57) ABSTRACT

Disclosed herein are striped dentifrice compositions stable to color bleeding comprising at least one zinc ion source and a thickening system comprising xanthan gum present in the composition in an amount ranging from about 0.3% to about 1% by weight and carboxymethyl cellulose present in the composition in an amount ranging from about 1% to about 2% by weight. Further disclosed herein are methods for cleaning the surface of a tooth comprising applying the striped dentifrice compositions stable to color bleeding as disclosed herein.

8 Claims, No Drawings

STRIPED DENTIFRICE COMPOSITION COMPRISING ZINC

BACKGROUND

Aesthetic effects of oral care compositions have been acknowledged to play significant effects on consumer acceptance and usage. The art seeks to further improve the aesthetic effects as well as the cosmetic and therapeutic benefits of these products. Indeed, many such compositions known in the art are deficient in one or more attributes.

Striped dentifrice products containing water-soluble dyes, for example, are known in the prior art. A major problem impacting the aesthetic appearance of striped toothpaste, however, is the bleeding or migration of color from one phase into another. When a water-soluble dye is used, the resultant product may have a low viscosity that will result in poor stripe definition. This may be especially severe if one colored component is applied to the surface of a white or lighter colored base. Bleeding may occur for a variety of reasons, one of which relates to an unacceptably low viscosity of the composition, for example due to the incorporation of water-soluble dyes, which may cause the colored phase to bleed into the white phase, for example.

Formulating a dentifrice composition with an acceptable rheology for striping may be problematic. When the content of water, which is a highly polar solvent, is reduced, conventional thickening agents such as carboxymethylcellulose ("CMC") tend to inadequately gel up. Non-aqueous formulations have been shown to exhibit progressive thickening over time, which prolongs the time period or even prevents the dentifrice from reaching a rheological steady state. Ideally, dentifrice formulations need to reach a steady state for consumer acceptance within two weeks. If a formulation routinely increases in viscosity over time, dispensing of the formulation will become difficult, which will likely result in consumer dissatisfaction. The rheology of the formulation should also be adequate for pumping and handling during the manufacturing process.

In addition to aesthetics, an oral care composition should also possess good therapeutic benefits, such as prevention of gum disease. Gum disease affects a significant number of people worldwide, and is a leading cause of tooth loss. Gum disease usually begins with gingivitis, in which bacteria in dental plaque build up, causing the gums to become inflamed. Dental plaque is a soft deposit that forms on teeth and is comprised of an accumulation of bacteria and bacterial by-products. Plaque adheres tenaciously at the points of irregularity or discontinuity, e.g., on rough calculus surfaces, at the gum line and the like. A wide variety of antibacterial agents have been suggested in the art to retard plaque formation. For example, halogenated hydroxydiphenyl ether compounds such as triclosan are well known in the art for their antibacterial activity and have been used in oral compositions to counter plaque formation by bacterial accumulation in the oral cavity. However, many people would prefer to use natural products such as natural salts such as zinc salts to provide antibacterial activity. The presence of these salts, however, may pose special challenges in formulating a toothpaste that has stable viscosity and good striping characteristics. Thus there is a need for novel dentifrice formulations possessing these characteristics.

BRIEF SUMMARY

Disclosed herein is an oral care composition, such as a multi-phase or striped dentifrice composition that is stable to color bleeding, comprising at least one zinc ion source; and a thickening system comprising a combination of xanthan gum present in the composition in an amount ranging from about 0.3% to about 1% by weight and carboxymethyl cellulose (CMC) present in the composition in an amount ranging from about 1% to about 2% by weight. In certain embodiments, the multi-phase dentifrice composition is free of triclosan, and in certain embodiments, the at least one zinc ion source is zinc citrate.

In various embodiments of the compositions disclosed herein, the xanthan gum is present in an amount ranging from about 0.3% to about 0.5%, such as about 0.3% by weight, and in certain embodiments, the CMC is present in an amount ranging from about 1% to about 1.5%, such about 1% by weight. In certain embodiments, the at least one zinc ion source is present in an amount ranging from about 0.01% to about 5% by weight, such as about 2% by weight.

In certain embodiments, the dentifrice compositions disclosed herein may further comprise at least one whitening agent, and in certain exemplary embodiments, the dentifrice compositions disclosed herein further comprise at least one silica abrasive, such as at least one small particle silica.

Also disclosed herein are methods for cleaning the surface of a tooth comprising applying a striped dentifrice composition stable to color bleeding comprising at least one zinc ion source and a thickening system comprising xanthan gum present in the composition in an amount ranging from about 0.3% to about 1% by weight and CMC present in the composition in an amount ranging from about 1% to about 2% by weight. In various exemplary embodiments of the disclosure, the at least one zinc ion source is zinc citrate. In certain embodiments, the xanthan gum is present in an amount of about 0.3% by weight, and in certain embodiments, the CMC is present in an amount of about 1% by weight.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiments is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

As used herein, the term "one or more of" with respect to a listing of items such as, for example, A and B, means A alone, B alone, or A and B. The term "at least one of" is used to mean one or more of the listed items can be selected.

Unless otherwise specified, all percentages and amounts expressed herein and elsewhere in the specification should be understood to refer to percentages by weight. The amounts given are based on the active weight of the material.

In certain embodiments disclosed herein, the oral care compositions may be in the form of a multi-phase dentifrice. A multi-phase dentifrice may comprise at least two visually distinguishable phases. The term "visually distinguishable phase" as used herein, refers to a region of a multi-phase composition having one average composition, as distinguishable from another region having a different average composition, wherein the regions are visible to the unaided naked eye. This would not preclude the distinguishable regions from comprising two similar compositions where one composition could comprise pigments, dyes, particles, and various optional ingredients, hence a region of a different average composition. For example, each composition could be the same except for a difference in pigment or dye, or each composition could be the same except for the particles.

In certain embodiments of a multi-phase dentifrice, the first dentifrice phase may be white and the second phase may be colored. It is an important aesthetic requirement for the consumer that the different phases (i.e., white and colored) have a sharp boundary between them and that the different colorants do not appear to bleed from one phase into the adjacent phase, as may occur, for example, when a water-soluble dye is used.

In certain embodiments, it may be effective to combine the at least two phases by first placing the separate compositions in separate storage tanks having a pump and a hose attached. The phases are then pumped into a single combining section. Next, the phases are moved from the combining sections into the filling section to form a filled product container that exhibits a visually distinguishable pattern of the phases. The pattern may be selected, for example, from striped, marbled, geometric, and mixtures thereof.

In order to establish the proper viscosity to create a multi-phase dentifrice composition having at least two visibly distinguishable phases, the dentifrice compositions disclosed herein may comprise at least one thickening system. The thickening system may be useful, in part, to give a desired consistency and/or mouth feel to the composition. The thickening system may also be useful to give the composition desirable handling and pumping characteristics in the manufacturing plant and during the manufacturing process. Any orally-acceptable thickening agent may be used in the thickening system, including, for example, carbomers, also known as carboxyvinyl polymers, carrageenans, also known as Irish moss, cellulosic polymers such as hydroxyethyl cellulose, carboxymethyl cellulose (CMC) and salts thereof, such as CMC sodium. Other exemplary thickening agents that may be mentioned include natural gums such as karaya, xanthan gum, gum arabic and tragacanth, colloidal magnesium aluminum silicate, colloidal silica, alginates, bentonite and other natural clays and synthetic inorganic clays, and the like. In one embodiment, the at least one thickening system comprises a combination of xanthan gum and CMC. In certain embodiments, the at least one thickening system comprises a combination of xanthan gum present in an amount ranging from about 0.3% to about 1%, such as about 0.5% to about 0.8%, and CMC present in an amount ranging from about 1% to about 2%, such as about 1% to about 1.5%. In certain embodiments, the at least one thickening system comprises a combination of xanthan gum present in an amount of about 0.3% and CMC present in an amount of about 1%.

In addition to the combination of xanthan gum and CMC, at least one additional thickening agent may be optionally present in the composition in a total amount ranging from about 0.01% to about 15%, such as from about 0.1% to about 10%, or from 0.2% to about 5%, by weight of the composition.

As one skilled in the art would recognize, properties of CMC may depend on the chain length of its cellulose backbone structure. Accordingly, in certain embodiments, use may be made of CMC comprising a backbone ranging from 8 to 12 cellulose units, such as 8 cellulose units (CMC8), 9 cellulose units (CMC9), or 12 cellulose units (CMC12).

The xanthan gum is polysaccharide having a molecular weight of about 1,000,000 to about 10,000,000. Xanthan has a primary structure consisting of regular repeating units, each containing five sugars: two glucose, two mannose, and one glucuronic acid. The main chain is built up of β-D-glucose units linked through the 1- and 4-positions, i.e., a chemical structure the same as cellulose. A three-sugar side chain is linked to the 3-position of every other glucose residue in the main chain. About half of the terminal D-mannose residues contain a pyruvic acid residue linked to the 4- and 6-positions.

Both CMC and xanthan gum contain carboxylate groups along their backbones. While both materials are charged polysaccharides, the density of charged carboxylate groups along the backbone is quite different, and much higher for the CMC than for the xanthan gum. For example, one known commercially available CMC, CMC 2000S (available from CPKelco) has a degree of substitution of about 0.9 carboxylate groups per sugar residue. Xanthan gum, in comparison, has a degree of substitution of <0.4 carboxylate groups per sugar residue. The number of carboxylate groups associated with the chain is important to the theological properties of a mixture that contains divalent ions such as $Zn^{2+}$ due to the fact that these ions complex with the carboxylate groups to form ionic crosslinks or bridges, with the zinc ions cross-linked to two opposing carboxylate groups.

In addition to the thickening system, the dentifrice compositions disclosed herein comprise at least one zinc compound that provides a source of zinc ions. Zinc ions have been found to help in the reduction of gingivitis, plaque, sensitivity, and improved breath benefits. Many zinc compounds, however, are sparingly soluble and hence must be used in relatively large amounts to provide an effective amount of zinc ions. Unfortunately, many zinc compounds also have an unpleasant consumer astringency, especially when used in relatively high concentration. The compositions disclosed herein allow for an effective incorporation of zinc ions into a dentifrice formulation. Examples of suitable zinc compounds that may serve as zinc ion sources include, for example, zinc oxide, zinc citrate, zinc sulfate, zinc chloride, zinc lactate, zinc gluconate, zinc malate, zinc tartrate, zinc carbonate, zinc phosphate, and other zinc salts. In certain embodiments, the zinc ion source is zinc citrate. In certain exemplary embodiments, the zinc citrate may be present in the composition in an amount ranging from about 0.01% to about 5%, such as about 0.1% to about 4%, about 1% to about 3%, or about 2% by weight.

The dentifrice compositions disclosed herein can further include one or more detergents or surfactants. Surfactants that may be mentioned in certain embodiments include, without limitation, anionic, nonionic, and amphoteric surfactants. Surfactants may be used, for example, to provide enhanced stability of the formulation, to help in cleaning the oral cavity surfaces through detergency, and to increase foaming of the composition upon agitation, e.g., during brushing. Suitable anionic surfactants include, for example, water-soluble salts of $C_{8-20}$ alkyl sulfates, sulfonated monoglycerides of $C_{8-20}$ fatty acids, sarcosinates and taurates; for example sodium lauryl sulfate, sodium coconut monoglyceride sulfonate, sodium lauryl sarcosinate, sodium lauryl isoethionate, sodium laureth carboxylate and sodium dodecyl benzenesulfonate, and mixtures thereof. Suitable nonionic surfactants include, for example, poloxamers, polyoxyethylene sorbitan esters, fatty alcohol ethoxylates, alkylphenol ethoxylates, tertiary amine oxides, tertiary phosphine oxides, dialkyl sulfoxides, and mixtures thereof. In one embodiment, the dentifrice disclosed herein comprises sodium lauryl sulfate, for example in an amount ranging from about 1% to about 10%, such as about 2% to about 8%, or about 5% by weight.

The dentifrice may also or alternatively comprise one or more nonpolar surfactants, for example polymers and copolymers of ethylene glycol and propylene glycol, e.g., poloxamers, i.e., nonionic triblock copolymers composed of a central hydrophobic chain of polyoxypropylene (poly(propylene oxide)) flanked by two hydrophilic chains of polyoxyethylene (poly(ethylene oxide)). The approximate lengths of the two PEG blocks may be, in some embodiments, an average of about 50-150 repeat units, e.g., about 100 repeat units while the approximate length of the propylene glycol block is an average of about 25-75 repeat units, e.g., about 50-60 repeat units. In one embodiments, the poloxamer may be poloxamer 407, also known by BASF tradename Pluronic® F127, which may be present in an amount ranging from about 0.5% to about 2%, such as about 1%, by weight.

In various embodiments, the dentifrice compositions disclosed herein may further comprise at least one whitening agent as a main active ingredient. In certain embodiments, the at least one whitening agent is a peroxide compound. As used herein, a "whitening agent" is a material which effects whitening of a tooth surface to which it is applied. As used herein, a "peroxide compound" is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxy phthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof.

Peroxide releasing compounds that may be mentioned for use in the dentifrice compositions disclosed herein include peroxide containing compounds such as urea peroxide, sodium percarbonate, sodium perborate and polyvinylpyrrolidone-$H_2O_2$ complexes (hereinafter "PVP-$H_2O_2$"). Polyvinylpyrrolidone is also known as poly-N-vinyl-poly-2-pyrrolidone and commonly abbreviated to "PVP". PVP generally refers to a polymer containing vinylpyrrolidone (also referred to as N-vinylpyrrolidone, N-vinyl-2-pyrrolidione and N-vinyl-2-pyrrolidinone) as a monomeric unit. The monomeric unit consists of a polar imide group, four non-polar methylene groups and a non-polar methane group.

Both linear and cross-linked complexes of PVP-$H_2O_2$ are known in the art, and PVP-$H_2O_2$ is considered to be stable in an anhydrous environment. Upon exposure to highly aqueous environments, such as in the oral cavity, the PVP-$H_2O_2$ dissociates into individual species (PVP polymer and $H_2O_2$). In one embodiment, the PVP-$H_2O_2$ complex is 80% by weight polyvinylpyrrolidone and 20% by weight $H_2O_2$.

In certain embodiments, the dentifrice composition may further comprise at least one agent to enhance release of the peroxide in the oral cavity as a part of the peroxide component whitening agent. POLY-PORE, which is an allyl methacrylate crosspolymer, available from Amcol health & Beauty Solutions, Inc., is an exemplary enhancing agent.

In various embodiments, the at least one whitening agent is present in the composition in an amount ranging from about 0.035% to 17.5%, such as from about 0.1% to about 10%, or from about 0.1% to about 6%, by weight relative to the total weight of the dentifrice composition.

In certain embodiments disclosed herein, the dentifrice composition may also comprise microcrystalline cellulose. It has been found that incorporating microcrystalline cellulose into aqueous dentifrice formulations may improve the flavor delivery and rheology profile as compared to a control toothpaste without microcrystalline cellulose. Microcrystalline cellulose is available from a variety of commercial sources. In one embodiment, the microcrystalline cellulose is provided as a blend of microcrystalline cellulose and sodium carboxymethyl cellulose, for example 80-90% microcrystalline cellulose and 10-20% sodium carboxymethyl cellulose (e.g., Avicel® CL611 from FMC BioPolymer (about 81.2%-88.7% microcrystalline cellulose and about 11.3-18.8% sodium carboxymethylcellulose).

In still further embodiments, the compositions disclosed herein comprise at least one humectant. Any orally acceptable humectant can be used, including without limitation, polyhydric alcohols such as glycerin, sorbitol, xylitol or low molecular weight polyethylene glycols. Many humectants also function as sweeteners. One or more humectants are optionally present in a total amount ranging from about 1% to about 70%, for example from about 5% to about 50%, from about 10% to about 40%, or from about 15% to about 30%, by weight based on the total weight of the composition.

In some embodiments the composition includes at least one anti-calculus agent. The at least one anti-calculus agent may be selected from, for example, a phosphate; a pyrophosphate; a polyphosphate; a phosphonate; a polyphosphonate; and mixtures thereof. In some embodiments, the pyrophosphate is selected from: a dialkali metal pyrophosphate salt; a tetra-alkali metal pyrophosphate salt; and mixtures thereof in their unhydrated as well as hydrated forms. Disodium dihydrogen pyrophosphate ($Na_2H_2P_2O_7$), tetrasodium pyrophosphate ($Na_4P_2O_7$) (TSPP), and tetrapotassium pyrophosphate ($K_4P_2O_7$) (TKPP) and mixtures thereof. Pyrophosphate salts suitable for use in the compositions of the present invention are described in more detail in Kirk and Othmer, Encyclopedia of Chemical Technology, 3rd Edition, Vol. 17, Wiley Interscience Publishers (1982). Additional anti-calculus agents include polyacrylates and other polycarboxylates; polyepoxysuccinates; ethylenediaminetetraacetic acid; nitrilotriacetic acid and related compounds; and polyphosphonates. Anticalculus phosphates include potassium and sodium pyrophosphates; sodium tripolyphosphate; diphosphonates such as ethane-1-hydroxy-1, 1-diphosphonate, 1-azacycloheptane-1, 1-diphosphonate, and linear alkyl diphosphonates; and linear carboxylic acids. The amount of anti-calculus agent optionally present in the composition of the invention is from about 0.1% to about 10%, by weight. In some embodiments, the anti-calculus agent is present in the amount of about 1% to about 5%, by weight.

In certain embodiments, the dentifrice compositions disclosed herein further comprise at least one colorant. Colorants may be used in a single-phase toothpaste or a multi-phase toothpaste for forming, for example, a striped toothpaste. In certain multi-phase dentifrice compositions disclosed herein, the composition comprises a first phase comprising a first colorant and a second phase comprising a second colorant. Colorants among those useful herein include pigments, dyes, lakes and agents imparting a particular luster or reflectivity such as pearling agents. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and mixtures thereof. One or more colorants are optionally present in a total amount of about 0.001% to about 20%, for example about 0.01% to about 10% or about 0.1% to about 5%. In certain embodiments, the at least one colorant for a first phase of a multi-phase dentifrice is titanium dioxide and the at least one colorant for a second phase of the multi-phase dentifrice is a different colorant other than titanium dioxide, such as a blue or green dye.

The compositions disclosed herein may also comprise at least one antimicrobial agent in addition to the at least one zinc ion source which may be selected from halogenated diphenyl ether (triclosan), herbal extracts or essential oils (e.g., rosemary extract, thymol, menthol, eucalyptol, methyl salicylate), bisguanide antiseptics (e.g., chlorhexidine, alexidine, or octenidine), phenolic antiseptics, hexetidine, povidone iodine, delmopinol, salifluor, sanguinarine, propolis, oxygenating agents (e.g., hydrogen peroxide, buffered sodium peroxyborate, or peroxycarbonate), cetyl pyridinium chloride, magnolia extract, magnolol, honokiol, butyl magnolol, propyl honokiol, substituted aminoalkans (e.g., N, N, N'-tris(2-hydroxyethyl)-N'-octadecyl-1,3-diaminopropane), and mixtures thereof. Anti-attachment agents such as Solrol also can be included, as well as plaque dispersing agents such as enzymes (papain, glucoamylase, etc.). In certain embodiments, the dentifrice compositions disclosed herein may be substantially free of triclosan. As used herein, substantially free of triclosan indicates that either no discernable triclosan is present or triclosan is present in such minimal quantities as to have no antimicrobial affect on the composition.

In some embodiments, the composition has a free water content of greater than about 10%, by weight. In some embodiments, the composition has a free water content of greater than about 15%, by weight. In other embodiments, the composition has a free water content of greater than about 20%, by weight. Yet other embodiments provide compositions wherein the free water content is greater than about 25%, by weight. Still other embodiments provide compositions having a free water content of greater than about 35%, by weight. In some embodiments, the composition has a free water content of from about 10% to about 50%, by weight, such as about 20% to about 40%, by weight.

In various embodiments of the present disclosure, the dentifrice compositions disclosed herein may have a basic pH, such as a pH greater than about 7, for example ranging from about 7 to about 9, or ranging from about 7.5 to about 8.5, such as a pH of about 8. In certain exemplary embodiments, the pH of the dentifrice composition may be adjusted with a base, such as sodium hydroxide or potassium hydroxide. In certain embodiments, the pH of the dentifrice composition may be adjusted with sodium hydroxide.

In certain embodiments, the compositions described herein can be used, for example, for cavity prevention, whitening, plaque prevention or reduction, gingivitis prevention or reduction, tartar control, breath malodor prevention or reduction, and stain prevention.

The dentifrice compositions disclosed herein may include an anionic polymer, for example in an amount of from about 0.05 to about 5%. Such agents are known generally for use in dentifrice, and include synthetic anionic polymeric polycarboxylates, such as 1:4 to 4:1 copolymers of maleic anhydride or acid with another polymerizable ethylenically unsaturated monomer, such as methyl vinyl ether/maleic anhydride having a molecular weight (M.W.) of about 30,000 to about 1,000,000, or about 300,000 to about 800,000. These copolymers are available for example as PVM/MA copolymers such as Gantrez®, e.g., AN 139 (M.W. 500,000), AN 119 (M.W. 250,000) and S-97 Pharmaceutical Grade (M.W. 700,000) available from ISP Technologies, Inc., Bound Brook, N.J. 08805. In certain embodiments the PVM/MA copolymers may be used as either a liquid or a powder. The enhancing agents when present may be present in amounts ranging from about 0.05% to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000. Another useful class of polymeric agents includes polyamino acids containing proportions of anionic surface-active amino acids such as aspartic acid, glutamic acid and phosphoserine.

In some embodiments, the dentifrice compositions disclosed herein include at least one abrasive, for example silica abrasives. The silica abrasives useful herein, as well as the other abrasives, generally have an average particle size ranging between about 0.1 and about 30 microns, such as about between 5 and about 15 microns. The silica abrasives can be from precipitated silica or silica gels, such as silica xerogels. Particular silica xerogels are marketed under the trade name SYLOID® by the W. R. Grace & Co., Davison Chemical Division. The precipitated silica materials may include those marketed by the J. M. Huber Corp. under the trade name ZEODENT®, including the silica carrying the designation ZEODENT® 115 and 119. Other useful abrasives that may be mentioned include sodium metaphosphate, potassium metaphosphate, aluminum silicate, calcined alumina, bentonite and other siliceous materials, and combinations thereof.

In some embodiments, the abrasive materials comprise a large fraction of very small particles, e.g., having a d50<5 microns, for example, small particle silica (SPS) having a d50 of about 3 to about 4 microns, for example SORBOSIL AC43® (Ineos). Such small particles may be particularly useful in formulations targeted at reducing hypersensitivity. The small particle component may be present in combination with a second larger particle abrasive. In certain embodiments, for example, the formulation comprises about 3 to about 8% SPS and about 25 to about 45% of a conventional abrasive. In certain embodiments, the dentifrice compositions disclosed herein comprise at least one small particle silica having a median particle size that is no greater than the average diameter of a human dentin tubule, such that one or more particles are capable of becoming lodged within the tubule, thereby effecting a reduction or elimination of perceived tooth sensitivity. In certain embodiments, the at least one small particle silica may be chosen from ZEODENT®, SIDENT®, SORBOSIL®, TIXOSIL®, and combinations thereof.

As previously described, many other components may further be included in the dentifrice compositions disclosed herein, and flavoring agents, sweetening agents, desensitizing agents, anti-microbial agents, anti-caries agents, anti-inflammatory agents, vitamins, enzymes, preservatives, and tartar control agents, for example.

In certain embodiments disclosed herein, for example, the dentifrice compositions may further comprise at least one flavoring agent. The at least one flavoring agent, may, for example, be selected from essential oils, as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint, spearmint and wintergreen. The flavoring agent may be incorporated in the compositions disclosed herein at a concentration ranging from 0.01% to about 2% by weight, such as about 0.1% to about 1% by weight.

In embodiments where the dentifrice composition is sweetened, at least one sweetening agent may be used as an alternative or as a complement to the at least one flavoring agent. Suitable sweetening agents may be water-soluble and include, for example, sodium saccharin, sodium cyclamate, xylitol, perillartien, D-tryptophan, aspartame, dihydrochalcones and the like. The at least one sweetening agent may be present in the composition in an amount ranging from about 0.01% to about 1% by weight, such as about 0.3% by weight.

Exemplary anti-inflammatory agents may include those typically used in oral care compositions, such as ibuprofen, flurbiprofen, aspirin, indomethacine. Exemplary anti-caries agents may include ingredients such as sodium-, calcium-, magnesium- and stannous fluoride, aminefluorides, disodium monofluorophosphate and sodium trimetaphosphate. Exemplary vitamins may include ingredients such as Vitamin C. Exemplary desensitizing agents may include ingredients such as potassium citrate, potassium chloride, potassium tartrate, potassium bicarbonate, potassium oxalate, potassium nitrate and strontium salts. Exemplary enzymes may include papain and glucoamylase.

The dentifrice compositions disclosed herein may also comprise at least one fluoride source. Fluoride-containing compounds have a beneficial effect on the care and hygiene of the oral cavity, e.g., diminution of enamel solubility in acid and protection of the teeth against decay. Examples of suitable fluoride sources include stannous fluoride, sodium fluoride, potassium fluoride, potassium stannous fluoride (SNFZ-KF), potassium fluorozirconate, sodium hexafluorostannate, stannous chlorfluoride, sodium monofluorophosphate (MFP), sodium fluorosilicate, ammonium fluorosilicate, amine fluoride, and ammonium fluoride. When present, the fluoride source may provide fluoride ions in amounts sufficient to supply about 25 ppm to about 25,000 ppm of fluoride ions, such as at least about 500 ppm, e.g., about 500 ppm to about 2000 ppm or about 1000 to about 1600 ppm. The appropriate level of fluoride will depend on the particular application. A toothpaste for general consumer use may typically have about 1000 ppm to about 1500 ppm, while pediatric toothpaste may have somewhat less. A dentifrice or coating for professional application could have as much as about 5,000 ppm or even about 25,000 ppm fluoride. The amount by weight of these materials, which dissociate or release fluoride or fluoride-containing ions, will depend on the molecular weight of the counterion as well as on the particular application, but suitably may be present in an effective but non-toxic amount, usually ranging from about 0.1% to about 2% by weight. In some embodiments, a fluoride source is selected from sodium fluoride, stannous fluoride, sodium monofluorophosphate and mixtures thereof. In some embodiments, the fluoride source is sodium fluoride, which may be present in the dentifrice compositions disclosed herein in an amount ranging from about 0.15% to about 0.5%, such as from about 0.2% to about 0.3%, by weight of the dentifrice composition.

In general, each of the foregoing adjuvants disclosed herein may be typically incorporated herein in any suitable amount, such as, for example, in amounts up to about 5%, provided they do not adversely affect the stability, viscosity, and cleansing properties of dentifrice composition disclosed herein.

EXAMPLES

Example 1

Laboratory Scale

Three different dentifrice formulations were prepared on a laboratory scale with varying amounts of xanthan gum and CMC as the thickening system. As shown below in Table 1, Formulation A contained 0.25% xanthan gum and 0.65% CMC; Formulation B contained 0.35% xanthan gum and 0.70% CMC; and Formulation C contained 0.3% xanthan gum and 1% CMC. It is to be noted that the formulations may be prepared with either liquid or powdered PVM/MA copolymer, and, as one of ordinary skill in the art would appreciate, the formulation adjusted accordingly (i.e., noting that in certain formulations of PVM/MA copolymers, approximately 1.5% of powdered PVM/MA copolymer is equivalent to approximately 9.09% liquid PVM/MA copolymer). Each of the formulations was prepared as a dual-phase dentifrice comprising a white phase and a colored phase, which contained identical formulations with the exception of a different coloring agent; the white phase (approximately 20%) and colored phase (approximately 80%) were then combined to create a striped, dual-phase dentifrice.

TABLE 1

Dentifrice Formulations A-C

| Ingredients | Formulation A % by weight | Formulation B % by weight | Formulation C % by weight |
|---|---|---|---|
| Sodium fluoride | 0.32% | 0.32% | 0.32% |
| Zinc citrate | 2.0% | 2.0% | 2.0% |
| Phosphate/ Pyrophosphate | 2.44% | 2.44% | 2.44% |
| PVM/MA copolymer | 1.5% | 1.5% | 1.5% |
| Sodium hydroxide | 1.25% | 1.25% | 1.25% |
| Silicas | 17.5% | 17.5% | 17.5% |
| Xanthan gum | 0.25% | 0.35% | 0.3% |
| CMC | 0.65% | 0.70% | 1.0% |
| Sodium lauryl sulfate | 1.9% | 1.9% | 1.9% |
| Water, fragrance, sweetener, colorant | QS | QS | QS |

Viscosity was measured for Formulations A, B and C over time, including at 2 hours, 24 hours, 1 week, 2 weeks, 3 weeks, and 4 weeks. The viscosity measurements are shown below in Table 2.

TABLE 2

Viscosity Results for Formulations

| Time | Formulation A | Formulation B | Formulation C |
|---|---|---|---|
| Initial | 50,000 cPs | 70,000 cPs | — |
| 2 hours | 85,000 cPs | 100,000 cPs | 165,000 cPs |
| 24 hours | 140,000 cPs | 300,000 cPs | 265,000 cPs |
| 1 week | 515,000 cPs | 540,000 cPs | 585,000 cPs |
| 2 weeks | 450,000 cPs | 560,000 cPs | 500,000 cPs |
| 3 weeks | 410,000 cPs | 490,000 cPs | 460,000 cPs |
| 4 weeks | 390,000 cPs | 510,000 cPs | 465,000 cPs |

It was determined that both Formulations B and C had acceptable viscosities at the laboratory scale, but the viscosity of Formulation A was unacceptably low. Moreover, the flavor of Formulation C was determined to be acceptable both initially and after 6 weeks.

The stripe quality was tested by extruding the striped toothpaste and visually evaluating the stripe quality. Formulation A failed striping on lab tests.

Example 2

Plant Scale

Based on the success of Formulations B and C from Example 1 above, the same formulations were prepared on the plant scale, rather than on the laboratory scale. As the plant uses different equipment, such as pumps, it was decided to run the scaled-up process on the formulations, because the pumps and other plant processes are known to influence the shearing and viscosities of the products. Therefore it is possible to observe lower viscosities in the samples produced in the plant versus samples produced in the laboratory. An undesirable viscosity (i.e., either too high or too low) may adversely affect the ease of handling and pumping of the product in the plant and during the manufacturing process. The viscosities of the plant formulations were tested over time and their striping characteristics evaluated as discussed above. Table 3 below shows the viscosity results for Formulations B and C when prepared at the plant scale.

TABLE 3

Viscosities of Formulations B and C at the Plant Scale

| Time | Formulation B | Formulation C |
|---|---|---|
| 2 hours | 70,000 cPs | 125,000 cPs |
| 24 hours | 95,000 cPs | 170,000 cPs |
| 1 week | 420,000 cPs | 620,000 cPs |
| 2 weeks | 310,000 cPs | 670,000 cPs |
| 3 weeks | 350,000 cPs | 655,000 cPs |
| 4 weeks | 350,000 cPs | 500,000 cPs |

Even though Formulation B performed well at the laboratory scale (See Example 1, above), the same formulation failed at the plant scale. The formulation resulted in a smooth cream that was free from lumps and air bubbles; however, poor striping resulted, as the product recovery time was not enough to provide good striping formation, resulting in failed striping definition. The slow viscosity build up for the formula was not enough to form the stripes properly. It was therefore concluded that the viscosity of the initially prepared colored and white bases at the plant scale was too low.

Formulation C resulted in a superior striped dentifrice product. The cream reached the ideal viscosity faster, and the striping quality was acceptable. The viscosity profile of Formulation C was enough to resist the plant's manufacturing conditions. Even though in the lab, both Formulations B and C produced good results, when tested in the plant environment, the increase in adjustment in thickening system concentration in the formulation impacted the final product quality.

What is claimed is:

1. A striped dentifrice composition stable to color bleeding comprising:
   at least one zinc ion source;
   at least one water-soluble color agent; and
   a thickening system comprising xanthan gum present in the composition in an amount of about 0.3% by weight and carboxymethyl cellulose present in the composition in an amount of about 1% by weight;
   wherein the at least one zinc ion source comprises zinc citrate, and wherein the zinc citrate is present at an amount of from 1% to 3% by weight, relative to the total weight of the striped dentifrice composition;
   wherein the striped dentifrice has a basic pH and wherein the pH is from about 7.5 to about 8.5;
   wherein the striped dentifrice is a multi-phase dentifrice, and the above-listed ingredients are present in the stated ranges within each phase of the striped dentifrice composition, wherein the composition is substantially free of triclosan, and wherein the composition exhibits a viscosity of about 500,000 cPs 4 weeks after production.

2. The striped dentifrice composition according to claim 1, wherein the carboxymethyl cellulose is present in an amount of 1% by weight.

3. The striped dentifrice composition according to claim 1, wherein the zinc citrate is present in an amount of about 2% by weight.

4. The striped dentifrice composition according to claim 1, further comprising at least one whitening agent.

5. The striped dentifrice composition according to claim 1, further comprising at least one silica abrasive.

6. The striped dentifrice composition according to claim 5, wherein the at least one silica abrasive is a small particle silica.

7. A method for cleaning a surface of a tooth comprising:
applying, to the surface, a striped dentifrice composition stable to color bleeding according to claim 1.

8. The striped dentifrice composition according to claim 1, wherein the zinc citrate is 2% by weight, relative to the total weight of the striped dentifrice composition.

* * * * *